(12) United States Patent
Cobelli et al.

(10) Patent No.: US 9,858,386 B2
(45) Date of Patent: Jan. 2, 2018

(54) METHOD TO RECALIBRATE CONTINUOUS GLUCOSE MONITORING DATA ON-LINE

(75) Inventors: Claudio Cobelli, Padua (IT); Giuseppe De Nicolao, Milan (IT); Andrea Facchinetti, Padua (IT); Stefania Guerra, Carre (IT); Giovanni Sparacino, Padua (IT)

(73) Assignee: Universita Degli Studi Di Padova, Padua (IT)

( * ) Notice: Subject to any disclaimer, the term of this patent is extended or adjusted under 35 U.S.C. 154(b) by 1171 days.

(21) Appl. No.: 13/504,858

(22) PCT Filed: Nov. 2, 2010

(86) PCT No.: PCT/IB2010/054947
§ 371 (c)(1),
(2), (4) Date: Apr. 27, 2012

(87) PCT Pub. No.: WO2011/051922
PCT Pub. Date: May 5, 2011

(65) Prior Publication Data
US 2012/0215087 A1  Aug. 23, 2012

Related U.S. Application Data

(60) Provisional application No. 61/257,288, filed on Nov. 2, 2009.

(51) Int. Cl.
*A61B 5/00* (2006.01)
*G06F 19/00* (2011.01)
(Continued)

(52) U.S. Cl.
CPC ........ *G06F 19/3412* (2013.01); *A61B 5/1495* (2013.01); *A61B 5/14532* (2013.01); *A61B 2560/0223* (2013.01)

(58) Field of Classification Search
CPC .......................... A61B 5/1495; A61B 5/14532
See application file for complete search history.

(56) References Cited

U.S. PATENT DOCUMENTS

2001/0016682 A1* 8/2001 Berner et al. ................. 600/345
2002/0045808 A1* 4/2002 Ford et al. .................... 600/347
(Continued)

OTHER PUBLICATIONS

Kosiborod, et al. Glucose Normalization and Outcomes in Patients With Acute Myocardial Infarction. Arch Intern Med. 2009;169(5):438-446. doi:10.1001/archinternmed.2008.593.*
(Continued)

*Primary Examiner* — Christian Jang
(74) *Attorney, Agent, or Firm* — Knobbe Martens Olson & Bear, LLP

(57) ABSTRACT

In a method of recalibrating continuous glucose monitoring data from a user, operable on a digital processor, an indication from the user that the user has taken a meal is received (806). A self-monitored of blood glucose levels from the user (810) at two separate times during a day corresponding to when the user has taken a meal. A glucose signal is received from a continuous glucose monitoring sensor (818) at times corresponding to the two separate times that the user has taken a meal. Two reconstructed blood glucose values based on the glucose signal from the continuous monitoring sensor at times when the at least two self-monitored of blood glucose levels are received from the user. A linear regression is performed (822) using y=ax+b, wherein x corresponds to the two reconstructed blood glucose values and y corresponds to the two self-monitored of blood glucose levels thereby generating an estimation of a and b. A recalibration signal, including the estimation of a and b, is transmitted to the continuous glucose monitoring sensor (824) based on the linear regression.

15 Claims, 5 Drawing Sheets

(51) Int. Cl.
  *A61B 5/145* (2006.01)
  *A61B 5/1495* (2006.01)

(56) References Cited

U.S. PATENT DOCUMENTS

| | | | | |
|---|---|---|---|---|
| 2002/0161288 | A1* | 10/2002 | Shin et al. | 600/316 |
| 2005/0027181 | A1* | 2/2005 | Goode et al. | 600/365 |
| 2005/0043598 | A1* | 2/2005 | Goode et al. | 600/316 |
| 2006/0015263 | A1* | 1/2006 | Stupp et al. | 702/19 |
| 2009/0156924 | A1 | 6/2009 | Shariati et al. | |
| 2009/0198118 | A1* | 8/2009 | Hayter et al. | 600/347 |

OTHER PUBLICATIONS

Facchinetti et al., Teconstruction of Glucose in Plasma from Interstitial Fluid Continuous Glucose Monitoring Data: Role of Sensor Calibration. J Diabetes Sci Technol., (2007) 1(5): 617-623.

Guerra et al.,. Enhancing the Accuracy of Subcutaneous Glucose Sensors: A Real-time Deconvolution-based Approach. IEEE Transactions on Biomedical Engineering. Mar. 23, 2012; 59(6): 1658-1669.

Guerra et al.,. Comparison of Four Methods for On-Line Calibration of CGM Data. Book of Abstracts, 9th Diabetes Technology Meeting (DTM), San Francisco (CA, USA), Nov. 5-7, 2009, 1 page.

Guerra et al.,. New Method for Recalibration of CGM Time-Series: Performance and Robustness Assessed by Simulation. Book of abstracts [308], 3rd International Conference on Advanced Technologies and Treatments for Diabetes (ATTD), Basel (Switzerland), Feb. 10-13, 2010, 3 pages.

International Search Report dated Aug. 11, 2011 for Application No. PCT/IB2010/054947, filed Nov. 2, 2010.

International Preliminary Report on Patentability and Written Opinion dated May 8, 2012 for Application No. PCT/IB2010/054947, filed Nov. 2, 2010.

\* cited by examiner

METHOD TO RECALIBRATE CONTINUOUS GLUCOSE MONITORING DATA ON-LINE

BACKGROUND OF THE INVENTION

Field of the Invention

The present invention relates to glucose monitoring systems and, more specifically, to a method of recalibrating continuous glucose monitoring data.

Description of the Prior Art

The standard therapy for diabetes is based on insulin and drug administration, diet, and physical exercise, tuned according to self-monitoring of blood glucose (SMBG) levels 3-4 times a day. However, given the inefficiency of SMBG approach in capturing the actual extent of glucose dynamics during the daily life, blood glucose concentration in diabetic patients often goes outside the normal range (70-180 mg/dl). In the last 10 years, new possibilities in diabetes therapy have been opened thanks to the availability of continuous glucose monitoring (CGM) sensors. CGM systems are noninvasive or minimally-invasive, and, in many cases, the fact that they are portable can allow their use in patient daily life for several days (up to a week).

Diabetes is a chronic disease characterized by the inefficiency of the pancreas to produce insulin (Type-1 diabetes), or by malfunctions in both insulin secretion and action (Type-2 diabetes). As a result, in a diabetic subject the plasma glycaemic level exceeds the normal range, with several long and short term complications. Diabetes is taking on epidemic proportions with over 220 million individuals affected by this disease worldwide (1 over 20 adults, 95% of whom have Type-2 diabetes), a number which is expected to grow to 366 million by the year 2030. The rapid, constant increase of diabetic patients make this disease one of the social-health emergencies of the third millennium. Most diabetics follow a metabolic monitoring therapy based on a combination of insulin injections and/or drugs, diet and physical exercise. The therapy is determined by the physician on the basis of glycaemia level measurements that the patient measures by him or herself in capillary blood 3 or 4 times a day (self-monitoring). This approach presents inevitable shortcomings due to the low amount of glycaemia data available related to the high glycaemia range during the day. Due to the shortcomings of the monitoring system, glycaemia may exceed normal limits (between 70 and 180 mg/dl). Hyperglycaemia (a situation in which the concentration of glucose in blood is higher than 180 mg/dl) causes various long-term complications (cardiovascular disease, hypertension, retinopathies, etc.), while on the short-term, hypoglycaemia (glucose concentration lower than 70 mg/dl) may even be more dangerous (e.g. it may lead to diabetic coma) also because it may be difficult for the patient to recognize, particularly at night.

New minimally invasive or in some cases not at all invasive devices for continuously monitoring glucose levels, known as Continuous Glucose Monitoring (CGM) devices, have been developed and marketed during the past years. CGM devices can compensate the lack of information of the traditional 3 or 4 Self Monitoring Blood Glucose (SMBG) measurements. In fact, they can measure, in real-time, the glycaemia level at a continuous time (from every 1 to 5 minutes, according to the sensor) for up to several days (from 3 to 7 days, according to the technology), allowing the improvement of diabetes management. Retrospective CGM data analysis (glycaemia level data can normally be downloaded by means of an appropriate software present in the device) may for example identify hypo/hyperglycaemic episodes which are not revealed by 3-4 daily measurements determined in capillary blood, and thus significantly help reviewing the specific patient's therapy. One of the features of CGM sensors is their capacity to estimate the current glucose level in real time. This makes them particularly interesting for recognizing potentially dangerous episodes in real time, such as exceeding of the aforesaid hypo/hyperglycaemic thresholds. For this reason, some CGM sensors are provided with alert generation methods, which warn the patient when the estimated glycaemia value exceeds predetermined thresholds.

Most of the commercialized CGM systems, e.g. the Seven® (DexCom Inc, San Diego, Calif.), the FreeStyle Navigator™ (Abbott Diabetes Care, Alameda, Calif.), and the CGMS® (Medtronic Minimed Inc, Northridge, Calif.), exploit the glucose-oxidase principle, which requires that the current levels (e.g. in mA) are transformed into glucose levels (e.g. mg/dl) by exploiting a transformation rule with parameters determined using one or more references, e.g. SMBG. This step is commonly referred to as a calibration. In addition, in order to reduce invasiveness, CGM sensors measure interstitial glucose (IG) rather than blood glucose (BG) concentration. In dynamic conditions, IG and BG differ because of the existence of a BG-to-IG kinetics.

To show this, FIG. 1 displays a comparison between BG references, collected every 15 minutes (measured with YSI, Yellow Springs, Ohio), and a CGM profile collected using a subcutaneous sensor (FreeStyle Navigator™, Abbott Diabetes Care, Alameda, Calif.) (these data were taken from the literature and are used for representative purposes only). Discrepancies between BG and CGM time series due to the BG-to-IG kinetics (e.g. amplitude and phase distortion) are rather evident.

BG-to-IG kinetics is usually described by the two-compartment model as shown in FIG. 2. From the model, BG and IG concentrations can be related through the following continuous-time differential equation:

$$\frac{dC_2(t)}{dt} = -(k_{02} + k_{12})C_2(t) + k_{21}\frac{V_1}{V_2}C_1(t) \quad (1)$$

where $C_1(t)$ and $C_2(t)$ are BG and IG concentration, respectively, $V_1$ and $V_2$ are BG and IG volumes, and $k_{ij}$ denote the transfer rate from compartment j to compartment i. Eq. (1) can be transformed in:

$$\frac{dC_2(t)}{dt} = -\frac{1}{\tau}C_2(t) + \frac{g}{\tau}C_1(t) \quad (2)$$

where $g=(k_{21}V_1/V_2)\tau$ and $\tau=1/(k_{02}k_{12})$. In summary, IG can be interpreted as the output of a first order linear system driven by BG, where g represents the "static gain" of the physiological BG-to-IG system (which we can consider equal to 1 without any loss of generality), and τ is the time constant of the system, which could vary between individuals. The system acts as a low-pass filter, and introduces a distortion (attenuation in amplitude and distortion in phase) which is well observable e.g. in time window 2-8 hours shown in FIG. 1.

The BG-to-IG kinetics is not able to explain the whole discrepancy between the CGM readings and the true plasma profile. An example of this fact can be inferred from FIG. 1, in the interval 25-33, where discrepancies which cannot be attributed to the physiological component can be visualized along the y-axis. In this case, we can see that the mean values of BG and CGM data are very different. This difference should be principally attributed to technological aspects and in particular to the change of behaviour of the CGM sensor performance after its initial calibration. Furthermore, by looking at FIG. 1, this source of error seems to have a time-varying nature, which has been modelled by [ref] as a multiplicative error in affecting sensor calibration.

The fact that CGM time series may differ from BG profiles because of calibration problems can be critical in several applications resorting to CGM sensors, e.g. artificial pancreas methods relying on CGM output. Real-time recalibration of CGM data is therefore an important task to deal with. Of note, these problems inevitably affect all the CGM traces, since a natural degradation of the sensor itself always occurs, but it is important to note that they can be recovered at a software level via a re-adjustment of the calibration that translates current readings into glucose concentration values.

Real-time recalibration of CGM sensors is hence necessary to increase the accuracy of their measurements. An accurate and precise CGM device can be extremely useful to improve the management of diabetes therapy, helping the patient in a tighter glucose concentration control, and hence reducing both long- and short-term complications.

Calibration is the most critical aspect in CGM devices. The calibration should transform the raw current level measured by the sensor into an IG level by exploiting one or more capillary BG measurements. The most adopted calibration strategy exploits is the so-called 2-point linear regression model reported in eq. (3)

$$y=ax+b \qquad (3)$$

where a and b are calibration parameters which are determined by fitting them against a couple of BG (y) and raw current CGM (x) levels collected at the same time. However, this procedure is less than suboptimal, because it does not take into account the distortion introduced by the BG-to-IG kinetics. In fact, by comparing BG and IG concentrations when glucose is changing rapidly, e.g. just after a meal, one could note that their level could be significantly different (e.g. 20 mg/dl). Therefore, drawing the calibration sample in such a point, i.e. while the raw current is not proportional to real BG level, could introduce a bias in CGM readings (e.g. in the 28-31 hour time interval of FIG. 1). In order to improve CGM accuracy, many other different recalibration procedures have been proposed in the literature.

A first attempt has been performed by DirecNet Study Group, which analyzed the improvement in CGMS sensor accuracy by retrospectively modifying the number and timing of the calibration points. Results evidenced the fact that the timing of the calibration points is even more important than the number. In particular, performing calibrations during periods of relative glucose stability, i.e. where the point-to-point difference due to the BG-to-IG kinetics is minimized, significantly improves the accuracy.

A second recalibration procedure is based on the same linear regression model of eq. (3), and works by exploiting all the BG references that one can have available. A first weak point of this procedure is that it can be applied only retrospectively. In addition, it does not take into account the BG-to-IG kinetics. Finally, it cannot deal with a possible time-varying behaviour of sensor performance (i.e. the parameters of eq. (3) are equal throughout the monitoring).

In another approach a dual-rate Kalman filter is presented to improve the accuracy of CGM data. The procedure exploits sparse SMBG measurements and estimates in real-time the sensor gain. A critical aspect of this algorithm is that it does not embed any BG-to-IG kinetics model. As a consequence, it is suboptimal because it considers SMBG and CGM measurements as if they were collected in the same site.

In a comprehensive description of the CGM measurement process, the BG-to-IG kinetics model was explicitly taken into account in order to reconstruct BG levels at continuous time from CGM measurements. To such a scope, a state-space Bayesian framework exploiting a priori knowledge of the unknown variables was adopted and an extended Kalman Filter (EKF) was implemented to perform state estimation.

In the most widely used technique for the recalibration of CGM profiles, a linear regression model is used to make two points of blood samples (see, e.g., FIG. 3) to match correspondent values of the original CGM trace sampled at the same time. This recalibration method (hereafter we will refer at this as gold standard) has been used to improve the accuracy of CGM time series is some recent studies.

Even if it is proved that this technique allows improving the quality of CGM traces, some important issues remain uncovered. In order to point out some of these open problems that cannot be faced with it, some simulated examples are here reported.

Example #1

In FIG. 3 shows data relative to the first simulation, i.e. the plasma glucose concentration (red line), inferred from 5 minute sampling traces, the interstitial glucose concentration, calculated feeding the plasma profile to the Rebrin BG-to-IG model, and the CGM profile, obtained multiplying the IG concentration by a profile which simulates a lack of calibration (in this example a non linear stretch of IG is used) and adding a measurement error. The CGM profile clearly suffers from lack of calibration. In order to recalibrate the data, the existing method is applied. Once the two pairs of measurements are collected (the two BG samples and the correspondent CGM data, see FIG. 3), the parameters of the linear regression of eq. (3) are calculated. Then, the whole CGM profile is adjusted by using the regression, obtaining the profile shown in FIG. 4. In this case, the gold standard technique performs satisfactorily. However, the gold standard technique is not robust. This can be shown with the following example.

Example #2

FIG. 5 shows data used in this second simulation. Applying the gold standard method by using the two pairs of values highlighted in the Figure, the recalibration leads to a large deviation from real data, even worse than the original CGM data. Results are displayed in FIG. 6.

The reason why the gold standard fails in recalibrating CGM data is due to the fact that the two pairs of values (i.e. the red and black circles) refer to two different compartments, i.e. BG and IG in FIG. 4. In fact, the whole BG-to-IG dynamic system acts like a filter, which has the effect of distorting and delaying the plasmatic profile. As a consequence, the IG concentration is a distorted and delayed version of BG. For this reason, if BG and IG concentrations are compared when glucose is changing rapidly, their level could be significantly different (e.g. 20 mg/dl). This is exactly the case of this second example. While in the first example the two points have been chosen when BG and IG levels are similar, in the second case the second of the two pairs have been selected during the rise up after the meal. If the BG-to-IG kinetics is not taken into account (as it happens in the gold standard procedure), this difference could be wrongly misread as a loss of accuracy of the sensor, introducing a bias in the estimation of the parameters of the regressor.

Therefore, any algorithm for the recalibration con CGM data which uses "inhomogeneous" quantities (i.e. BG and IG) for the estimation of its parameters should not ignore the dynamics between them.

It is currently believed that all the up-to-date available methods for recalibration use both CGM and BG values without considering any BG-to-IG kinetics.

The inclusion of a model of the BG-to-IG dynamic system can improve CGM recalibration algorithms, making them more physiology-aware, with great benefit for the precision of CGM devices.

Most of the CGM devices exploit the glucose-oxidase principle, i.e. they measure, within the subcutaneous tissue, an electrical current, proportional to the glucose level in the interstitium, which is then converted into a glucose level in an "internal" calibration step (which requires suitable blood glucose (BG) references taken at times empirically determined). However, in practical situations, a possible deterioration of sensor gain may occur, which leads the CGM output to be significantly different from the true glucose profile. Especially in real-time applications, this calls for CGM recalibration algorithms.

Existing state-of-the-art recalibration algorithms present several limitations. In particular, they do not take into account that: a) CGM devices measure glucose into the interstitium compartment rather than into the blood compartment where the reference BG samples are taken; b) the times at which reference BG samples are collected for calibration should be accurately determined by means of exhaustive computer simulations; c) CGM sensors accuracy may change in time, and calibration should be continuously reassessed. As a consequence of a), b) and c), the recalibration provided by the state-of-the-art methods is suboptimal.

Therefore, there is a need for a device that includes a recalibration algorithm that explicitly takes into account: the physiology of the signals into play and, in particular, the existence of a plasma-to-interstitium glucose kinetics; the possibility of including the reference BG sampling times among the design variables; and the possible time-varying behavior of the sensor accuracy.

SUMMARY OF THE INVENTION

The disadvantages of the prior art are overcome by the present invention which, in one aspect, is a system employing an algorithm that can be described as it follows. A deconvolution procedure is employed (by using the sensor CGM signal and a "population" impulse response) to reconstruct a profile which is then scaled, by means of a regression model, in order to fit the available reference BG samples (at least two). Optimal times at which these BG references should be collected by the patient are suggested from the algorithm (on the basis of an exhaustive numerical simulation made in the phase of algorithm design). Once the parameters of the regressor have been estimated, the measured CGM data are recalibrated by employing the regressor itself. In order to track possible changes in the sensor performance, the recalibration algorithm can be launched every time a new pair of reference BG samples is available (e.g. typically twice a day, at breakfast and at dinner).

The new algorithm works on-line. Numerical simulations demonstrate that it is largely superior to the state-of-the-art algorithms, in terms of both accuracy and robustness One embodiment of the invention here proposed includes in a recalibration method, which aims to a dynamics-aware on-line recovering of CGM data, in order to obtain a more accurate and precise glucose concentration. The invention can either be embedded in a commercialized CGM device or be a part of a separate system, which receives CGM data as input and returns the recalibrated CGM data as output. The algorithm recalibrates CGM readings comparing values which belong to the same compartment. In fact, BG and CGM data is typically not directly compared, because of the distortion introduced by the BG-to-IG dynamics. Thanks to the exploitation of a model describing the BG-to-IG dynamic system, the invention converts CGM data into BG concentration before comparing it with BG references collected for calibrating the device.

The algorithm which is part of the invention receives as inputs:
 the CGM readings;
 the time of meals;
 population parameters describing the BG-to-IG dynamics of the system;
 some SMBG references (at least 2);
 the time in which SMBG references have been collected.

The inputs required by the algorithm are compatible with every CGM device which exploits one or more SMBG to be calibrated. In addition, the calibration procedure we propose can be used in series with the CGM device (see FIG. 9): the raw CGM signal is fed to the calibration module, that will calibrate it exploiting only some simple input information from the patient (SMBG and meal announcements). The information provided by the patient is perfectly compatible with standard self monitoring he or she is used to perform, in fact, only few (4 per day) SMBG samples are required.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAILED DESCRIPTION OF THE INVENTION

Figure 1:
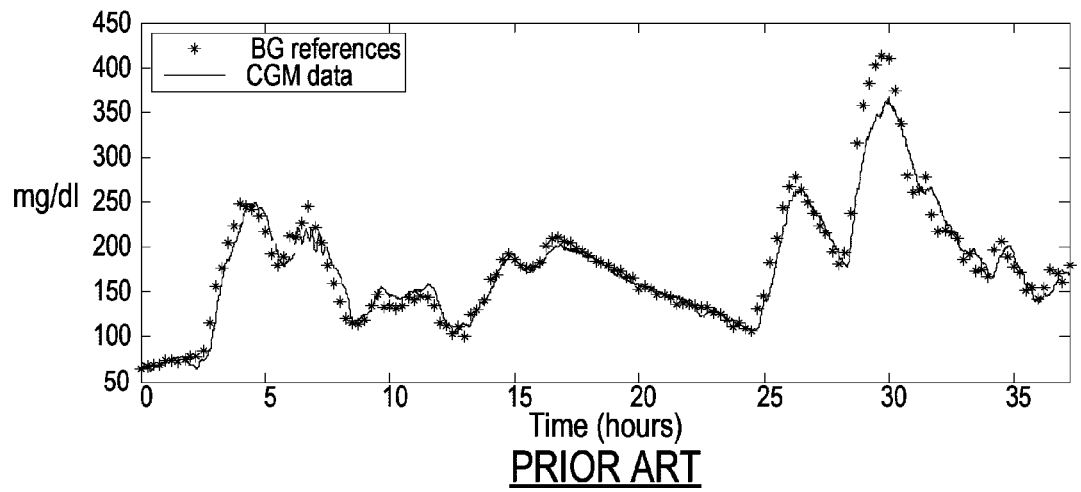
FIG. 1 is a graph relating BG references to CGM data profiles.
Figure 2:
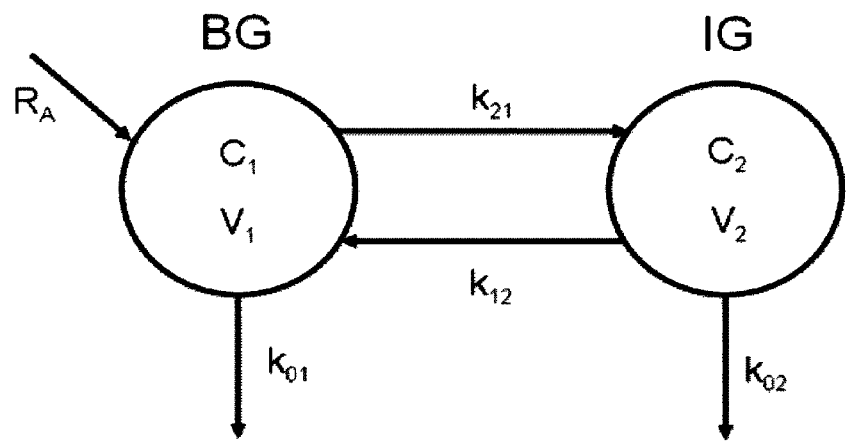
FIG. 2 is a two-compartmental model describing relationship and exchanges between BG (compartment 1) and IG (compartment 2) concentrations.

A preferred embodiment of the invention is now described in detail. Referring to the drawings, like numbers indicate like parts throughout the views. Unless otherwise specifically indicated in the disclosure that follows, the drawings are not necessarily drawn to scale. As used in the description herein and throughout the claims, the following terms take the meanings explicitly associated herein, unless the context clearly dictates otherwise: the meaning of "a," "an," and "the" includes plural reference, the meaning of "in" includes "in" and "on." Also, as used herein, "global computer network" includes the Internet.

A recalibration method for dynamics-aware on-line recovering of CGM data is configured to obtain a more accurate and precise glucose concentration. Either be embedded in a commercialized CGM device or be a part of a separate system, which receives CGM data as input and returns the recalibrated CGM data as output, the algorithm recalibrates CGM readings comparing values which belong to the same compartment. BG and CGM data cannot be directly compared, because of the distortion introduced by the BG-to-IG dynamics. Employing a model describing the BG-to-IG dynamic system, the method converts CGM data into BG concentration before comparing it with BG references collected for calibrating the device.

Figure 7:
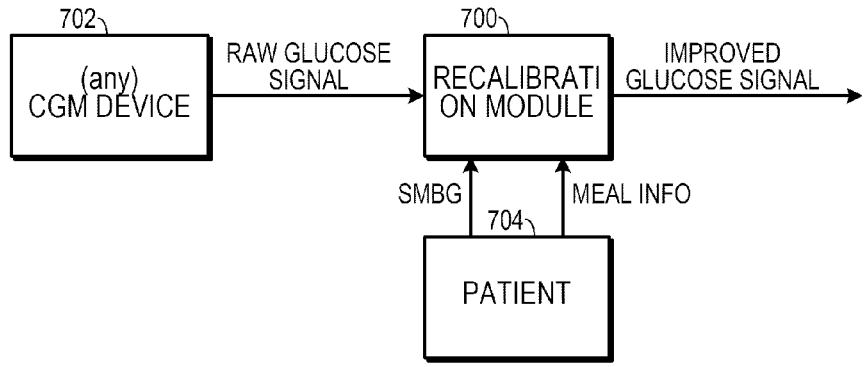
FIG. 7 is a schematic diagram showing one embodiment of a recalibration module and input information that has to be inserted by the patient.

As shown in FIG. 7, one embodiment includes a calibration module 700 that receives a raw glucose signal from a continuous glucose monitoring device 702 and that receives both meal information and self monitored blood glucose data from a patient 704. The recalibration module 700 would typically be executable on a digital computer and the data from the patient 704 could be received by the processor via the global computer network.

The recalibration method part of the invention leans on a linear regression which exploits two pairs of glucose measures. The first pair consists of two reference BG measures (e.g. SMBG, received in input), the second pair consists of two reconstructed blood glucose (RBG) values, obtained converting the CGM data (received in input) into a "potential" plasma glucose concentration. exploiting the BG-to-IG kinetics and a deconvolution procedure. In details, the recalibration algorithm works as follow:

Measurements received from the CGM device are stored;

CGM data is converted into RBG data, which can have theoretically generated it, by exploiting a deconvolution procedure based on a dynamic model of the BG-to-IG system (the parameters of the BG-to-IG model can be either individual or population parameters);

Two RBG values are extracted from the RBG profiles in correspondence to the times in which the two BG references have been collected;

The parameters (a,b) of a linear regressor $y=ax+b$ are estimated by using as x data the pair of RBG and as y data the pair of BG;

The regressor is hence used to recalibrate in real time CGM data, obtaining new CGM data as output of the system. new $CGM=aCGM+b$ With this procedure, the couples of measures which are used inside eq. (3) (above) belong to the same compartment, i.e. BG, and therefore the estimation of the parameters of eq. (3) is performed among "homogeneous" quantities. As it has been described in the last point of the procedure, once the parameters of the regressor are obtained, the regressor can be on-line applied to the original CGM traces (thanks to the linearity of the whole system) to obtain in real time the new recalibrated profile.

Figure 8:
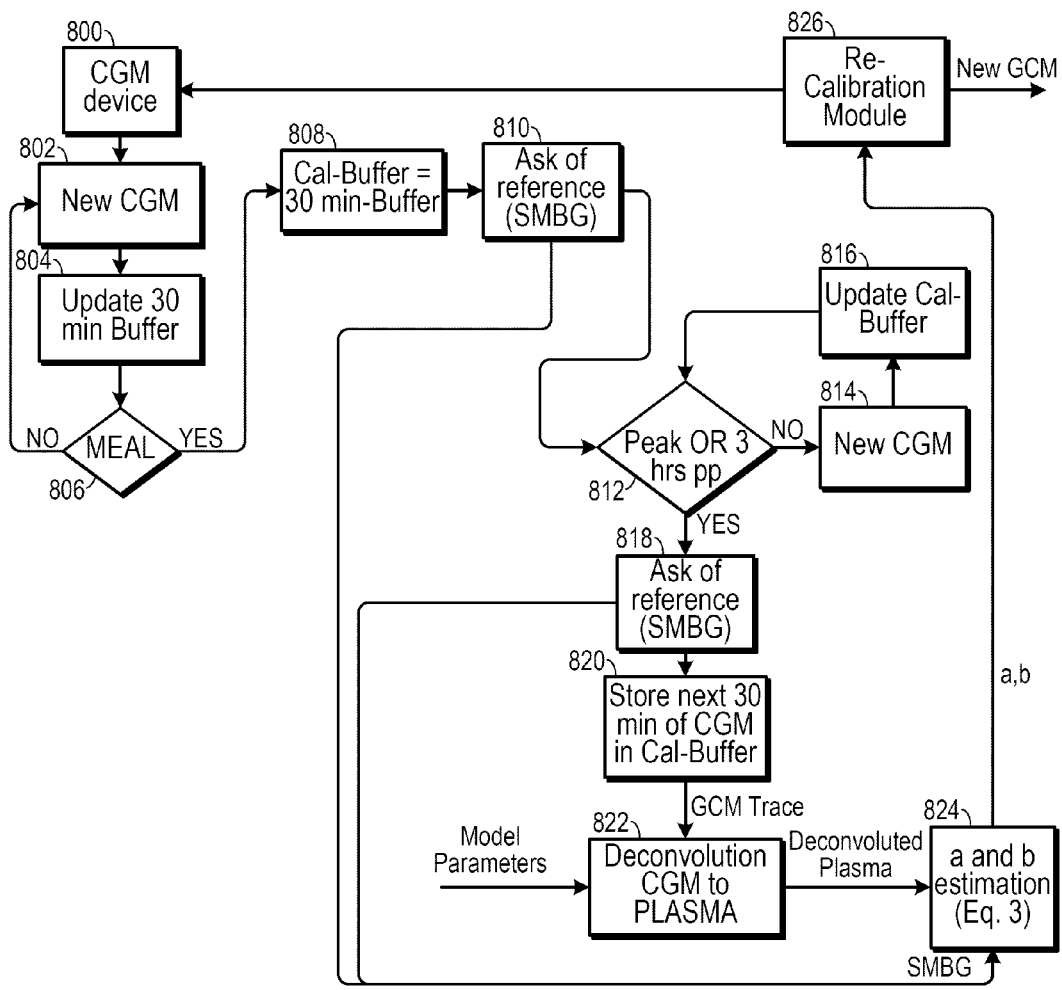
FIG. 8 is a flowchart describing one procedure for recalibration.

A flowchart describing the suggested procedure for the recalibration with dynamics-aware tool is shown in FIG. 8. Starting from the CGM data stream 800 (e.g. a new glucose value every 1 or 5 minutes 802), the algorithm buffers at least 30 minutes of data 804 (the buffer must be updated at each new incoming measure). If no meal announcement arrives 806, the algorithm keeps on updating the buffer 804 at each measure 802. When a meal is announced (information that must be given in input by the patient), the algorithm stores the actual 30-minute-buffer in the so called Cal-Buffer 808, which stores the trace of CGM we intend to use for deconvolution purposes. As soon as a meal is announced, a SMBG reference is required (patient dependent input) 810. The SMBG value should be given in input by the patient in the 10-minute window after it is required; otherwise the recalibration procedure is aborted. After meal the algorithm stores every new CGM value 814 in the Cal-Buffer 816 until a postprandial peak is reached OR for a maximum of 3 hours after the meal 812 if the postprandial peak has not yet been reached. When one of the two conditions is satisfied, the patient is asked for a second SMBG reference 818. The SMBG value has to be given in input by the patient in the 10-minute window after it is requested, otherwise the recalibration procedure is aborted. Information about SMBG is stored 820, as well as the Cal-Buffer, which is updated for the 30 minutes following the collection of the second SMBG. Then, the "theoretical" plasma profile that should have generated the CGM data till here stored is reconstructed by exploiting a deconvolution based procedure 822, which uses a BG-to-IG kinetics model (individualized or population parameters can be used) to take into account the distortion of the dynamics between the two compartments. SMBG and corresponding deconvoluted plasma values are fed to the linear regression to estimate the correction parameters 824 (such as that shown in Equation 3, above), which in turn are fed to the CGM device or to the final user of the CGM trace, who will be able to correct the original CGM data.

There could be many different model-based procedures to reconstruct a plasmatic profile from CGM readings. Here, two possible procedures are shown: the first performs a parametric deconvolution by exploiting a polynomial-based model, the second performs a non-parametric deconvolution; both are based on literature state-of-art BG-to-IG model, exploiting individual/population values for the model parameters. The two algorithms here suggested can be easily performed online, since they yield a close-form solution. The whole calibration process is then condensed in a chain of matrix products.

Figure 3:
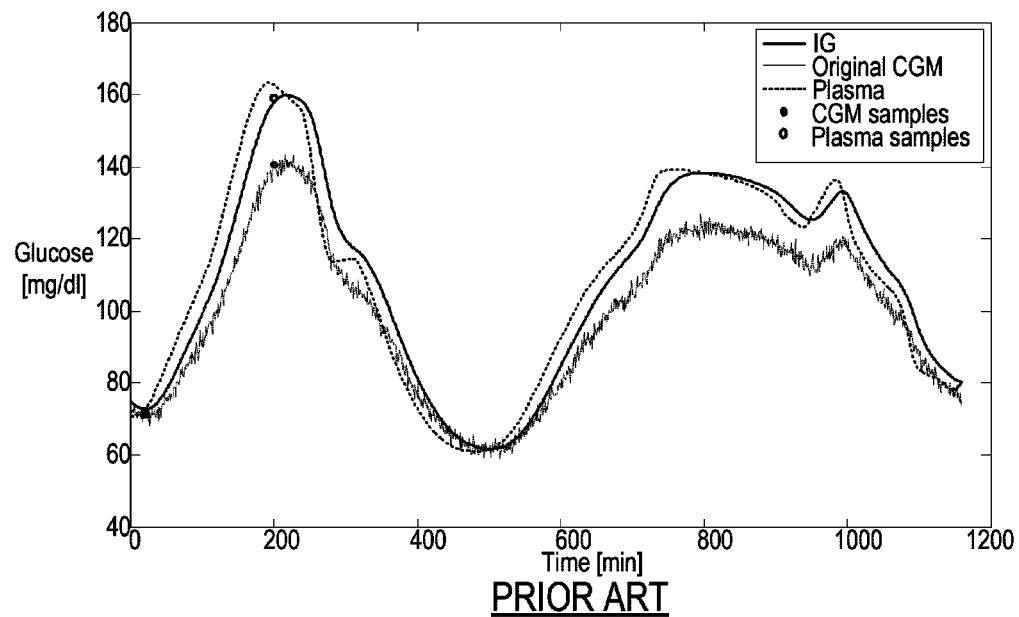
FIG. 3 is a graph showing BG, IG, and CGM values, respectively, including two pairs of values selected and used for recalibrating CGM data with the gold standard method.
Figure 4:
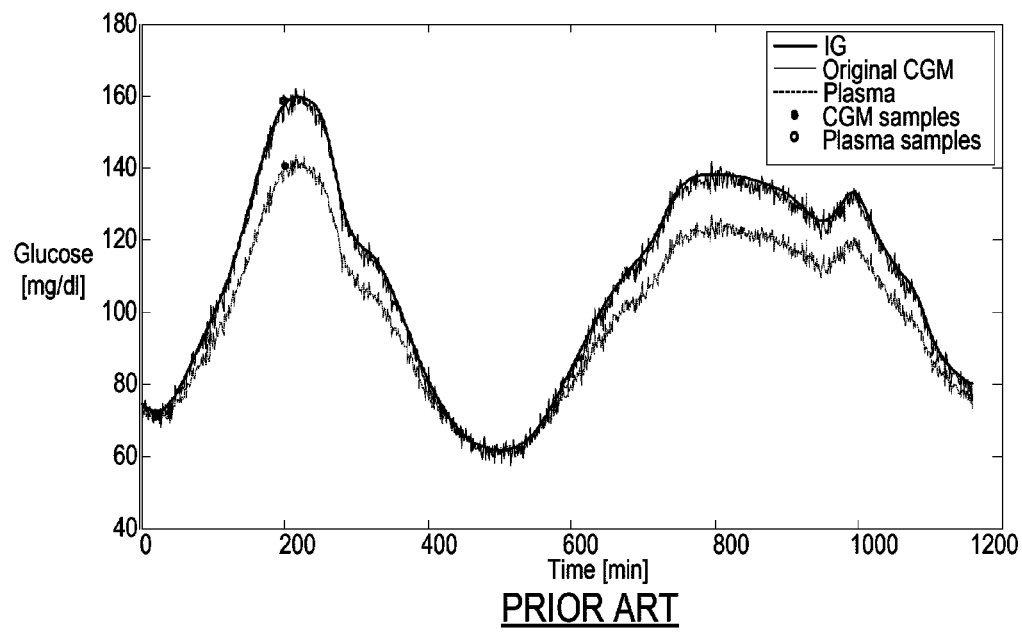
FIG. 4 is a graph showing results of the application of the gold standard to recalibrate CGM data showing true IG and CGM data and recalibrated CGM by using the gold standard and the two pairs of values.
Figure 5:
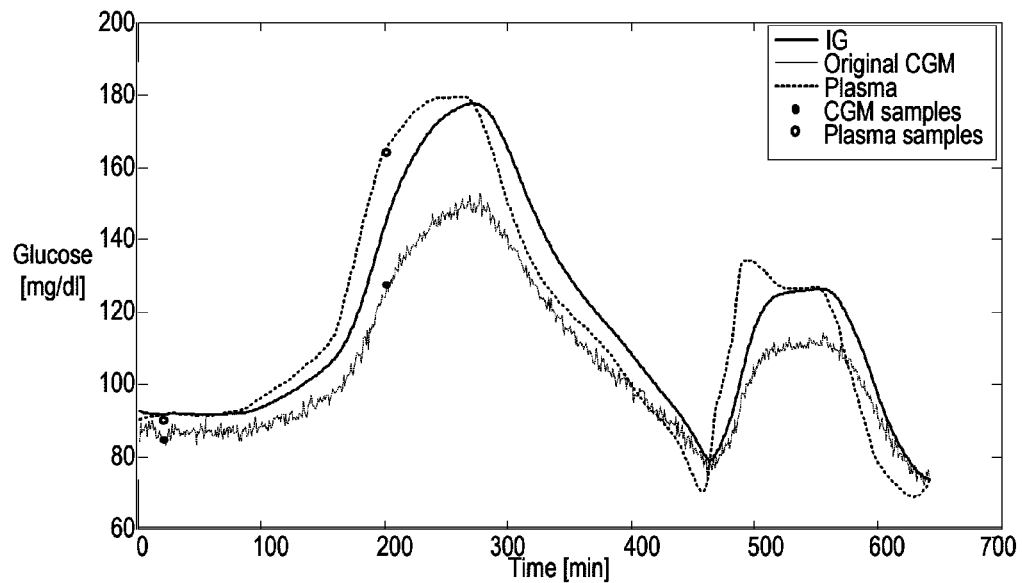
FIG. 5 is a graph showing data used in Example #2.
Figure 6:
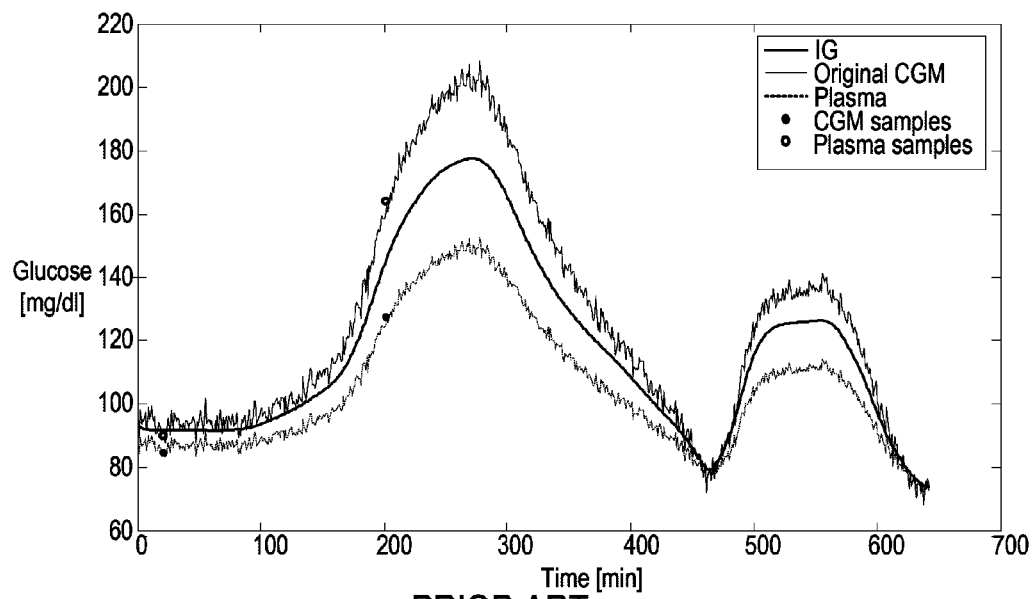
FIG. 6 is a graph showing Results of the application of the gold standard to recalibrate CGM data.
Figure 9:
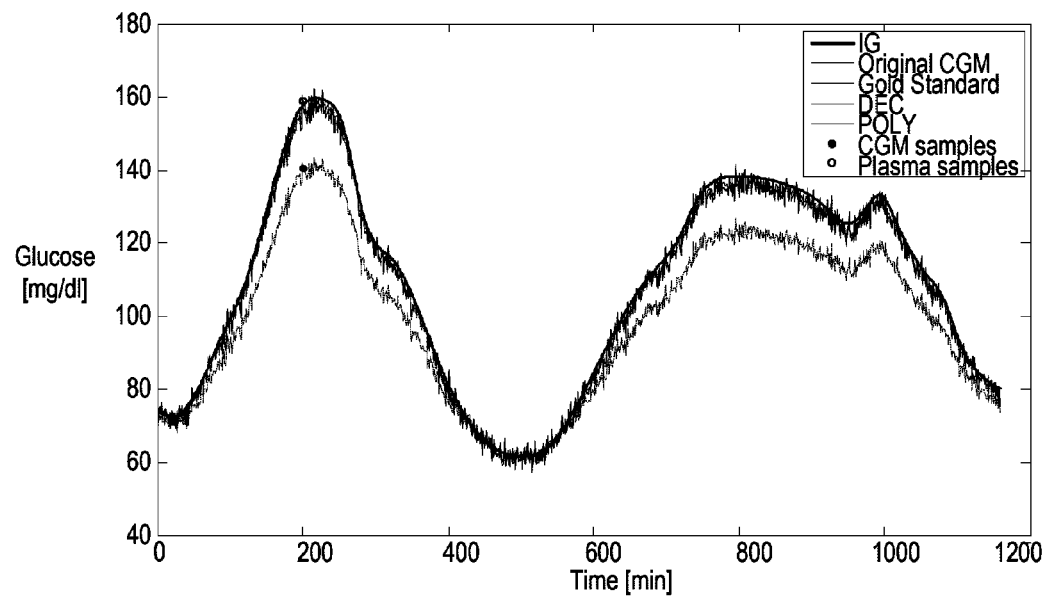
FIG. 9 is a graph showing results of the application of the gold standard and model-based recalibration techniques to recalibrate CGM data of Example #1.
Figure 10:
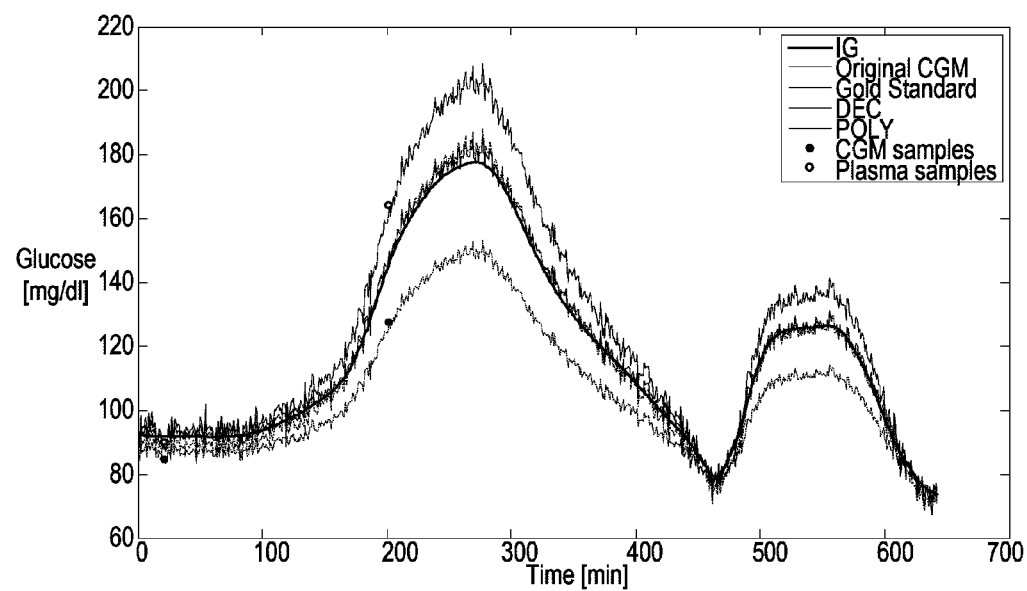
FIG. 10 is a graph showing results of the application of the gold standard and model-based recalibration techniques to recalibrate CGM data of Example #2.

FIGS. 9 and 10 show results of the application of the two new recalibration methods on the simulated examples seen in FIGS. 3 and 5. In both simulations, both methods provide a satisfactory recalibration profiles significantly better than the one obtained by using the gold standard (the "POLY" and the "DEC" profiles are obtained by using the polynomial-based parametric deconvolution and the non-parametric deconvolution recalibration approaches, respectively).

CGM devices may lead to fundamental improvement for the management of diabetes, since they can provide an insight on glycaemic trends. Their high-frequent information can be fed to control and prediction systems for the optimal management of the disease. However, CGM sensor accuracy is not always satisfactory because of both the degradation of sensor performance during the whole monitoring and possibly bad-calibration of the device. On-line recalibration of CGM sensors becomes a crucial issue for the correction of these technology-relates problems and for the improvement of sensors performance.

Many different recalibration algorithms have proposed in the CGM field literature. The most used is able to improve the accuracy of CGM readings by exploiting a linear regressor which parameters are estimated by comparing two BG references and the corresponding measured CGM data; however this procedure is not stable, because in many situations it produces a CGM value which is even less accurate than original. The inability of improving CGM data accuracy is due to the fact that the procedure ignores the dynamic system that correlates IG to BG concentrations, which acts as a low-pass filter, distorting the IG concentration. If one of the recalibration points is collected e.g. on a rising front of glucose concentration, BG and IG point-to-point difference could be even higher than 15/20 mg/dl. If the BG-to-IG kinetics is not taken into account, this difference could be wrongly considered as a loss of accuracy of the sensor, introducing a bias in the estimation of the parameters of the regressor. It is important to note that likely all state-of-the-art methods try to match these inhomogeneous quantities (i.e. IG and BG), hence suffering from dynamics related problems.

The recalibration method here proposed is able to improve CGM data accuracy in all situations, because it embeds a model of the BG-to-IG kinetics. In fact, first the "theoretical" plasma glucose concentration that could have generated CGM data is reconstructed by using a deconvolution-based procedure and a model of the BG-to-IG kinetics, and then the parameters of the linear regressor are estimated. In this way, the estimation is performed comparing homogeneous quantities, i.e. BG references (e.g. a pair of SMBG measurements) and the correspondent RBG samples taken from the reconstructed plasma profile. The limitation of state-of-the-art recalibration procedures is overcome, and the possibility of obtaining a recalibrated CGM value worse than original CGM data is avoided.

One of the most important features of this new method is that it works on-line. Once the parameters of the regressor have been estimated, the regressor can be directly applied to original CGM data, adjusting their values.

The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:
1. A system for recalibrating continuous glucose monitoring data from a user, comprising:
   a. a processor;
   b. a continuous glucose monitoring sensor, in communication with the processor, configured to provide data to generate a glucose signal of continuously monitored glucose values representing interstitial glucose values; and
   c. a recalibration module, configured to:
      i. receive an indication that the user has taken a meal;
      ii. receive at least two self-monitored blood glucose levels corresponding to separate times after the user has taken the meal;
      iii. receive the glucose signal from the continuous glucose monitoring sensor;
      iv. generate reconstructed blood glucose values indicative of plasma glucose concentration values by converting at least some of the glucose signal representing interstitial glucose values into a plasma glucose concentration signal;
      v. select at least two reconstructed blood glucose values among the generated reconstructed blood glucose values corresponding to times associated with the at least two self-monitored blood glucose levels;
      vi. generate a first parameter and a second parameter by performing a linear regression using the at least two selected reconstructed blood glucose values and the at least two self-monitored blood glucose levels; and
      vii. produce a recalibration signal of the continuously monitored glucose values using the first parameter and the second parameter.

2. The system of claim 1, wherein the calibration module is configured to convert the at least some of the glucose signal into the plasma glucose concentration signal with a deconvolution procedure based on a dynamic model of a blood glucose to interstitial glucose system.

3. The system of claim 1, wherein the calibration module is configured to generate a request to the user for a self monitored blood glucose level at a first predetermined period after the user has had the meal.

4. The system of claim 3, wherein the first predetermined period comprises thirty minutes.

5. The system of claim 4, wherein the calibration module is configured to generate a request to the user for a self monitored blood glucose level at a second predetermined period after the user has had the meal.

6. The system of claim 5, wherein the second predetermined period comprises three hours.

7. The system of claim 1, wherein the processor and the continuous glucose monitoring sensor are in communication with each other via a global computer network.

8. The system of claim 1, wherein the recalibration module is further configured to execute each day after the user has taken two different meals.

9. A method of recalibrating continuous glucose monitoring data from a user, operable on a processor, comprising:
   a. receiving from a receiver an indication that the user has taken a meal;
   b. receiving from the receiver at least two self-monitored blood glucose levels corresponding to separate times after the user has taken the meal;
   c. receiving a glucose signal of continuously monitored glucose values representing interstitial glucose values obtained from a continuous glucose monitoring sensor;
   d. generating reconstructed blood glucose values indicative of plasma glucose concentration values by converting at least some of the glucose signal representing interstitial glucose values into a plasma glucose concentration signal;

e. selecting at least two reconstructed blood glucose values among the generated reconstructed blood glucose values corresponding to times associated with the at least two self-monitored blood glucose levels;

f. generating a first parameter and a second parameter by performing a linear regression using the at least two selected reconstructed blood glucose values and the at least two self-monitored blood glucose levels; and g. producing a recalibration signal of the continuously monitored glucose values using the first parameter and the second parameter.

10. The method of claim 9, wherein the converting the at least some of the glucose signal into the plasma glucose concentration signal includes using a deconvolution procedure based on a dynamic model of a blood glucose to interstitial glucose system.

11. The method of claim 9, further comprising generating a request to the user for a self monitored blood glucose level at a first predetermined period after the user has had the meal.

12. The method of claim 11, wherein the first predetermined period comprises thirty minutes.

13. The method of claim 12, further comprising generating a request to the user for a self monitored blood glucose level at a second predetermined period after the user has had the meal.

14. The method of claim 13, wherein the second predetermined period comprises three hours.

15. The method of claim 9, further comprising communicating data from the continuous glucose monitoring sensor to the processor and from the processor to the continuous glucose monitoring sensor via a global computer network.

* * * * *